United States Patent [19]
Santos et al.

[11] Patent Number: 5,955,096
[45] Date of Patent: Sep. 21, 1999

[54] METHODS AND COMPOSITIONS FOR ENHANCING THE BIOADHESIVE PROPERTIES OF POLYMERS USING ORGANIC EXCIPIENTS

[75] Inventors: Camila A. Santos, Newport, R.I.; Jules S. Jacob, Taunton, Mass.; Benjamin A. Hertzog; Gerardo P. Carino, both of Providence, R.I.; Edith Mathiowitz, Brookline, Mass.

[73] Assignee: Brown University Research Foundation, Providence, R.I.

[*] Notice: This patent issued on a continued prosecution application filed under 37 CFR 1.53(d), and is subject to the twenty year patent term provisions of 35 U.S.C. 154(a)(2).

[21] Appl. No.: 08/670,326

[22] Filed: Jun. 25, 1996

[51] Int. Cl.[6] .............................. C08G 67/04; A61K 9/00; A61F 2/00

[52] U.S. Cl. ........................... 424/434; 424/486; 424/491; 424/497; 424/499; 523/105; 523/113; 528/271; 528/272; 525/165; 525/419

[58] Field of Search .................................... 424/434, 491, 424/498; 528/271; 523/105, 113; 525/419

[56] References Cited

U.S. PATENT DOCUMENTS

| | | | |
|---|---|---|---|
| 2,675,619 | 4/1954 | Cone | 33/449 |
| 2,677,700 | 5/1954 | Jackson et al. | 568/618 |
| 2,979,578 | 4/1961 | Curtis | 200/196 |
| 3,036,118 | 5/1962 | Jackson et al. | 560/182 |
| 3,535,307 | 10/1970 | Moss et al. | 536/18.3 |
| 3,829,506 | 8/1974 | Schmolka et al. | 568/624 |
| 4,757,128 | 7/1988 | Domb et al. | 528/271 |
| 4,861,627 | 8/1989 | Mathiowitz et al. | 427/213.31 |
| 4,938,763 | 7/1990 | Dunn et al. | 600/37 |
| 4,976,968 | 12/1990 | Steiner | 424/491 |
| 4,997,904 | 3/1991 | Domb | 424/426 |
| 5,019,400 | 5/1991 | Gombotz et al. | 424/497 |
| 5,173,298 | 12/1992 | Meadows | 424/427 |
| 5,175,235 | 12/1992 | Domb et al. | 528/271 |
| 5,271,961 | 12/1993 | Mathiowitz et al. | 424/491 |
| 5,474,768 | 12/1995 | Robinson | 424/78.31 |
| 5,518,731 | 5/1996 | Meadows | 424/427 |
| 5,611,344 | 3/1997 | Bernstein et al. | 424/673 |

FOREIGN PATENT DOCUMENTS

| | | |
|---|---|---|
| 0 333 523 A2 | 9/1989 | European Pat. Off. . |
| 91/06286 | 5/1991 | WIPO . |
| 91/06287 | 5/1991 | WIPO . |
| WO 92/11871 A1 | 7/1992 | WIPO . |
| 93/21906 | 11/1993 | WIPO . |

OTHER PUBLICATIONS

Beck, et al., "A new long–acting injectable microcapsule system for the administration of progesterone," *Fertil. & Steril.*, 31(5):545–55 (1979).

Benita, et al., "Characterization of drug loaded poly(d, l–lactide) microspheres," *J. Pharm. Sci.*, 73(12):1721–24 (1984).

Chickering & Mathiowitz, "Bioadhesive microspheres: I. A novel electrobalance–based method to study adhesive interactions between individual microspheres and intestinal mucosa," *J. Control. Release* 34:251–61 (1995).

Duchêne, et al., "Pharmaceutical and medical aspects of bioadhesive systems for drug administration," *Drug Dev. & Ind. Pharm.*, 14(2&3):283–318 (1988).

Edelman, et al., "Perivascular and intravenous administration of basic fibroblast growth factor: Vascular and solid organ deposition," *Proc. Natl. Acad. Sci., USA* 30:1513–17 (1993).

Gurney, et al., "Bioadhesive intraoral release systems: design, testing and analysis," *Biomaterials*, 5:336–40 (1984).

Harada, et al., "Basic fibroblast growth factor improves myocardial function in chronically ischemic porcine hearts," *J. Clin. Invest.*, 94(2):623–30 (1994).

Horowitz, M., "Mucopolysaccharides and Glycoproteins of the Alimentary Tract," *Handbood of Physiology* (C.F. Code, ed.), pp. 1063–85 (American Physiological Society 1967).

Labat–Robert & Decaeus, "Glycoprotèine du mucus gastrique: structure, fonctions et pathologie," *Pathologie et Biologie*, 24:241 (Paris 1979).

Labhasetwar, et al., "Sotalol Controlled release systems for arrhythmias: In vitro characterization, in vivo drug disposition, and electophysiologic effects," *J. Pharm. Sci.*, 83(2):156–64 (1994).
Lehr, et al., "Intestinal transit of bioadhesive microspheres in an situ loop in the rat—a comparative study with copolymers and blends based on poly(acrylic acid)," *J. Controlled Rel.*, 13:51–62 (1990).
Li & Li, "Use of Enzymes in Elucidation of Structure," *The Glycoconjugates* (Horowitz, ed.), pp. 51–67 (Academic Press 1977).
Mathiowitz, et al., "Novel Microcapcules for delivery systems," *Reactive Polymers*, 6:275–83 (1987).
Mathiowitz, et al., "Morphology of polyanhydride microsphere delivery systems," *J. Scanning Microscopy*, 4(2):329–40 (1990).
Mikos, et al., "Interaction of polymer microspheres with mucin gels as a means of characterizing polymer retention on mucus," *J. Colloid & Interfact Sci.*, 143(2):366–73 (1991).
Park, et al., "Alternative Approaches to Oral Controlled Drug Delivery: Bioadhesives and In–Situ Systems" *Recent Advances in Drug Delivery Systems* (Aderson & Kim, eds.), pp. 163–83 (Plenum Press 1983?).
Smart, et al., "An in vitro investigation of mucosa–adhesive materials for use in controlled drug deliver" *J. Pharm. & Pharmacol.*, 36:295–99 (1984).
Spiro, R., "Glycoproteins," *Annual Review of Biochemistry*, 39:599–638 (Snell, ed. 1970).
Tutwiler, et al., "A pharmacologic profile of McN–3495 [N–(1–methyl–2–pyrrolidinylidene)–N–pheyyl–1–pyrrolidinecarboxyimidamide], a new orally effective hypoglycemic agent," *Diabetes*, 27:(8):856–67 (1978).

*Primary Examiner*—Tae Yoon
*Attorney, Agent, or Firm*—Arnall Golden & Gregory LLP

[57] ABSTRACT

Methods and compositions are provided for enhancing the bioadhesive properties of polymers used in drug delivery systems. The bioadhesive properties of a polymer are enhanced by incorporating an anhydride oligomer into the polymer to enhance the ability of the polymer to adhere to a tissue surface such as a mucosal membrane. Anhydride oligomers which enhance the bioadhesive properties of a polymer include oligomers synthesized from dicarboxylic acid monomers, preferably those found in Krebs glycolysis cycle, especially fumaric acid. The oligomers can be incorporated within a wide range of polymers including proteins, polysaccharides and synthetic biocompatible polymers. In one embodiment, anhydride oligomers can be incorporated within polymers used to form or coat drug delivery systems, such as microspheres, which contain a drug or diagnostic agent. The oligomers can either be solubilized and blended with the polymer before manufacture or else used as a coating with polymers over existing systems. The polymers, for example in the form of microspheres, have improved ability to adhere to mucosal membranes, and thus can be used to deliver a drug or diagnostic agent via any of a range of mucosal membrane surfaces including those of the gastrointestinal, respiratory, excretory and reproductive tracts.

32 Claims, 1 Drawing Sheet

METHODS AND COMPOSITIONS FOR ENHANCING THE BIOADHESIVE PROPERTIES OF POLYMERS USING ORGANIC EXCIPIENTS

BACKGROUND OF THE INVENTION

The present invention is generally in the area of polymeric drug delivery systems.

Controlled release systems for drug delivery are often designed to administer drugs in specific areas of the body. In the case of drug delivery via the gastrointestinal tract, it is critical that the drug not be delivered substantially beyond the desired site of action and eliminated before it has had a chance to exert a topical effect or to pass into the bloodstream. If a drug delivery system can be made to adhere to the lining of the appropriate viscus, its contents will be delivered to the targeted tissue as a function of proximity and duration of contact.

An orally ingested product can adhere to either the epithelial surface or the mucus lining of the gastrointestinal tract. For the delivery of bioactive substances, it can be advantageous to have a polymeric drug delivery device adhere to the epithelium or to the mucous layer. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups.

Several microsphere formulations have been proposed as a means for oral drug delivery. These formulations generally serve to protect the encapsulated compound and to deliver the compound into the blood stream. Enteric coated formulations have been widely used for many years to protect drugs administered orally from stomach acid, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 523 by The UAB Research Foundation and Southern Research Institute. EPA 0 333 523 describes microparticles of less than ten microns in diameter that contain antigens, for use in oral administration of vaccines. The microparticles are formed of polymers such as poly(lactide-co-glycolide), poly(glycolide), polyorthoesters, poly(esteramides), polyhydroxybutyric acid and polyanhydrides, and are absorbed through the Peyer's Patches in the intestine, principally as a function of size.

Duchene et al., *Drug Dev. Ind. Pharm.*, 14:283–318 (1988) is a review of the pharmaceutical and medical aspects of bioadhesive systems for drug delivery. Polycarbophils and acrylic acid polymers were noted as having the best adhesive properties. "Bioadhesion" is defined as the ability of a material to adhere to a biological tissue for an extended period of time. Bioadhesion is clearly one solution to the problem of inadequate residence time resulting from the stomach emptying and intestinal peristalsis, and from displacement by ciliary movement. For sufficient bioadhesion to occur, an intimate contact must exist between the bioadhesive and the receptor tissue, the bioadhesive must penetrate into the crevice of the tissue surface and/or mucus, and mechanical, electrostatic, or chemical bonds must form. Bioadhesive properties of polymers are affected by both the nature of the polymer and by the nature of the surrounding media.

Others have explored the use of bioadhesive polymers. PCT WO 93/21906 discloses methods for fabricating bioadhesive microspheres and for measuring bioadhesive forces between microspheres and selected segments of the gastrointestinal tract in vitro. Smart et al., *J. Pharm. Pharmacol.*, 36:295–299 (1984), reports a method to test adhesion to mucosa using a polymer coated glass plate contacting a dish of mucosa. A variety of polymeric materials were tested, including sodium alginate, sodium carboxymethyl-cellulose, gelatin, pectin and polyvinylpyrrolidone. Gurney et al., *Biomaterials*, 5:336–340 (1984) reported that adhesion may be affected by physical or mechanical bonds; secondary chemical bonds; and/or primary, ionic or covalent bonds. Park et al., "Alternative Approaches to Oral Controlled Drug Delivery: Bioadhesives and In-Situ Systems,38 in J. M. Anderson and S. W. Kim, Eds., "Recent Advances in Drug Delivery," Plenum Press, New York, 1984, pp. 163–183, reported a study of the use of fluorescent probes in cells to determine adhesiveness of polymers to mucin/epithelial surface, which indicated that anionic polymers with high charge density appear to be preferred as adhesive polymers.

Mikos et al., in *J. Colloid Interface Sci.*, 143:366–373 (1991) and Lehr et al., *J. Controlled Rel. Soc.*, 13:51–62 (1990) reported a study of the bioadhesive properties of polyanhydrides and polyacrylic acid, respectively, in drug delivery. Lehr et al. screened microparticles formed of copolymers of acrylic acid using an in vitro system and determined that the copolymer "Polycarbophil" has increased adhesion.

In general, gastrointestinal (GI) mucus is made of 95% water and 5% electrolytes, lipids, proteins and glycoproteins, as described by Spiro, R. G., *Annual Review of Biochemistry,* 39:599–638 (1970); Labat-Robert, J. and Decaeus, C., *Pathologie et Biologie* (Paris), 24:241 (1979); and Horowitz, M. I., "Mucopolysaccharides and Glycoproteins of the Alimentary Tract" in *Alimentary Canal* (Eds. C. F. Code), pp. 1063–1085 (Washington: American Physiological Society, 1967).

There is a need for methods for controlling or increasing the absorption of pharmaceutical agents from polymeric drug delivery systems such as polymeric microspheres through mucosal membranes. There also is a need for methods for delaying transit of the systems through nasal or gastrointestinal passages. It is therefore an object of the present invention to provide methods for improving the bioadhesive properties of polymeric drug delivery systems such as microspheres, tablets, capsules and stents. It is another object of the invention to provide methods for improving the adhesion of drug delivery systems such as microspheres to mucosal membranes including buccal and nasal membranes and membranes of the gastrointestinal and reproductive tracts. It is a further object of the invention to provide polymeric drug delivery systems with improved ability to bind to mucosal membranes which can be used to deliver a wide range of drugs or diagnostic agents in a wide variety of therapeutic applications. Another object of the invention is to provide polymeric drug delivery systems with improved ability for uptake across the intestinal mucosa, wherein the particles of the drug delivery system are in the size range of 0.1–10 μm.

SUMMARY OF THE INVENTION

Polymers with enhanced bioadhesive properties are provided wherein anhydride monomers or oligomers are incorporated into the polymer. The polymers may be used to form drug delivery systems which have improved ability to adhere to tissue surfaces, such as mucosal membranes. The anhydride oligomers are formed from organic diacid monomers, preferably the diacids normally found in the Krebs glycolysis cycle. Anhydride oligomers which enhance the bioadhesive properties of a polymer have a molecular weight of about 5000 or less, typically between about 100 and 5000 daltons, or include 20 or fewer diacid units linked by anhydride linkages and terminating in an anhydride linkage with a carboxylic acid monomer.

The oligomer excipients can be blended or incorporated into a wide range of hydrophilic and hydrophobic polymers including proteins, polysaccharides and synthetic biocompatible polymers. In one embodiment, oligomers can be incorporated within polymers used to form or coat drug delivery systems, such as microspheres, which contain a drug or diagnostic agent. In another embodiment, oligomers with suitable molecular weight may be used alone to encapsulate therapeutic or diagnostic agents. In yet another embodiment, anhydride oligomers may be combined with metal oxide particles to improve bioadhesion even more than with the organic additives alone. Organic dyes because of their electronic charge and hydrophobicity/hydrophilicity can either increase or decrease the bioadhesive properties of polymers when incorporated into the polymers.

The polymers, for example in the form of microspheres, have increased ability to adhere to mucosal membranes, and thus can be used to deliver a drug or diagnostic agent via any of a range of mucosal membrane surfaces including those of the gastrointestinal, respiratory, excretory and reproductive tracts.

DETAILED DESCRIPTION OF THE INVENTION

Figure 1:
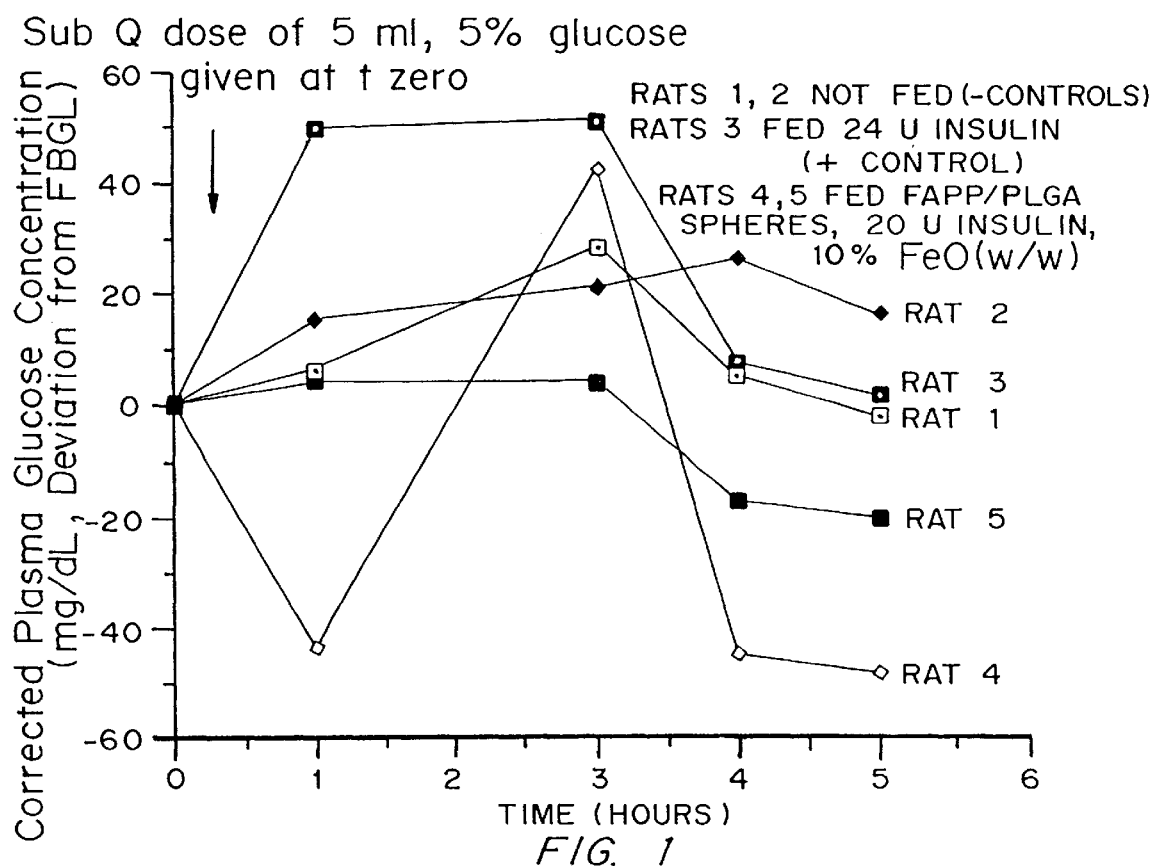
FIG. 1 is a graph comparing blood glucose levels in rats after administration of insulin in a saline solution and in fumaric acid oligomers/poly(lactide-co-glycolide) microspheres containing FeO.

Polymers having an anhydride oligomer incorporated therein are provided which have an increased adherence to tissue surfaces, such as mucosal membranes. The oligomer incorporated into the polymer can be, for example, an anhydride oligomer of poly fumaric, poly sebacic or poly maleic acid with methylated or "blocked" end groups. In one embodiment, the polymers can be used to form drug delivery systems, such as polymeric microspheres, containing a therapeutic or diagnostic agent. The incorporation of oligomer compounds into a wide range of different polymers which are not normally bioadhesive dramatically increases their adherence to tissue surfaces such as mucosal membranes. The polymers incorporating the oligomer compound can be used to form a wide variety of drug delivery systems, such as polymeric microspheres, which can be used to deliver therapeutic and diagnostic agents to mucosal membranes throughout the body including the gastrointestinal, excretory, respiratory and reproductive tracts. The oligomer compounds can be incorporated into polymers forming or coating tablets, osmotic pumps, or any device capable of interacting with mucosal membranes. Additionally, metal oxides can be incorporated along with the oligomers to further increase the bioadhesive properties of the polymer.

Anhydride Oligomers

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 daltons, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile. As analyzed by gel permeation chromatography, the molecular weight may be, for example, on the order of 200–400 for fumaric acid oligomer (FAPP) and 2000–4000 for sebacic acid oligomer (SAPP). The anhydride bonds can be detected by Fourier transform infrared spectroscopy by the characteristic double peak at 1750 $cm^{-1}$ and 1820 $cm^{-1}$, with a corresponding disappearance of the carboxylic acid peak normally at 1700 $cm^{-1}$.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic Dyes

Organic dyes, because of their electronic charge and hydrophilicity/hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2, 3, 13 and 86, rose bengal, safranin o, Sudan III and IV, Sudan black B and toluidine blue.

Polymers

Anhydride oligomers and organic dyes can be incorporated by dissolving, dispersing, or blending into a wide range of different polymers to improve the ability of the polymers to bind to tissue. For example, oligomers can be incorporated into polymers used to form or coat drug delivery systems such as polymeric microspheres.

Representative polymers which can be used include hydrophilic polymers, such as those containing carboxylic groups, including polyacrylic acid. Bioerodible polymers including polyanhydrides, and poly hydroxy acids) and polyesters, as well as blends and copolymers thereof also can be used. Representative bioerodible poly(hydroxy acids) and copolymers thereof which can be used include poly (lactic acid), poly(glycolic acid), poly(hydroxy-butyric acid), poly(hydroxyvaleric acid), poly(caprolactone), poly (lactide-co-caprolactone), and poly(lactide-co-glycolide). Polymers containing labile bonds, such as polyanhydrides and polyorthoesters, can be used optionally in a modified form with reduced hydrolytic reactivity. Positively charged hydrogels, such as chitosan, and thermoplastic polymers, such as polystyrene, also can be used.

Representative natural polymers which also can be used include proteins, such as zein, modified zein, casein, gelatin, gluten, serum albumin, or collagen, and polysaccharides such as dextrans, polyhyaluronic acid and alginic acid. Representative synthetic polymers include polyphosphazenes, polyamides, polycarbonates, polyacrylamides, polysiloxanes, polyurethanes and copolymers thereof. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt.

Polymers of acrylic and methacrylic acids or esters and copolymers thereof can be used. Representative polymers which can be used include poly(methyl methacrylate), poly (ethyl methacrylate), poly(butyl methacrylate), poly (isobutyl methacrylate), poly(hexyl methacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate).

Other polymers which can be used include polyalkylenes such as polyethylene and polypropylene; polyarylalkylenes such as polystyrene; poly(alkylene glycols), such as poly (ethylene glycol); poly(alkylene oxides), such as poly (ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly (vinyl acetate), polyvinyl phenol and polyvinylpyrrolidone.

Polymers which alter viscosity as a function of temperature or shear or other physical forces also may be used. Poly(oxyalkylene) polymers and copolymers such as poly (ethylene oxide)-poly(propylene oxide) (PEO-PPO) or poly (ethylene oxide)-poly(butylene oxide) (PEO-PBO) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained. For example, polyoxyalkylene copolymers, such as copolymers of polyoxyethylene and polyoxypropylene are described in U.S. Pat. Nos. 3,829, 506; 3,535,307; 3,036,118; 2,979,578; 2,677,700; and 2,675, 619, the disclosures of which are incorporated herein.

Polyoxyalkylene copolymers are sold, for example, by BASF under the tradename Pluronics™. These materials are applied as viscous solutions at room temperature or lower which solidify at the higher body temperature. Other materials with this behavior are known in the art, and can be utilized as described herein. These include Klucel™ (hydroxypropyl cellulose), and purified konjac glucomannan gum.

Polymer solutions that are liquid at an elevated temperature but solid or gelled at body temperature can also be utilized. A variety of thermoreversible polymers are known, including natural gel-forming materials such as agarose, agar, furcellaran, beta-carrageenan, beta-1,3-glucans such as curdlan, gelatin, or polyoxyalkylene containing compounds, as described above. Specific examples include thermosetting biodegradable polymers for in vivo use described in U.S. Pat. No. 4,938,763 to Dunn, et al., the teachings of which are incorporated herein.

These polymers can be obtained from sources such as Sigma Chemical Co., St. Louis, Mo. Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

Formation of Polymeric Microspheres

A wide variety of polymers can be used to form microspheres, wherein the polymer surface of the microsphere has incorporated therein an anhydride oligomer which enhances bioadhesive properties of the microsphere, such as the ability of the microsphere to adhere to mucosal membranes. The oligomers which enhance the bioadhesive properties of the polymers preferably are incorporated from a oligomer/polymer ratio of 0.1% to 95% into the polymer before formation of the microspheres. As used herein, the term "microspheres" includes microspheres having a uniform spherical shape, microcapsules (having a core and an outer layer of polymer) and particles of irregular shape. Generally, the microspheres have a diameter from the nanometer range up to about 5 mm. The microsphere may consist entirely of polymer incorporating a polyanhydride oligomer or can have only an outer coating of polymer incorporating the oligomer.

In one embodiment, polylactic acid microspheres can be fabricated using methods including solvent evaporation, hot-melt microencapsulation and spray drying. Polyanhydrides made of bis-carboxyphenoxypropane and sebacic acid or poly(fumaric-co-sebacic) can be prepared by hot-melt microencapsulation. Polystyrene microspheres can be prepared by solvent evaporation. Hydrogel microspheres can be prepared by dripping a polymer solution, such as alginate, chitosan, alginate/polyethylenimine (PEI) and carboxymethyl cellulose (CMC), from a reservoir though microdroplet forming device into a stirred ionic bath, as disclosed in PCT WO 93/21906, published Nov. 11, 1993, the disclosure of which is incorporated herein by reference.

The anhydride oligomers can be incorporated into the polymeric microspheres either before or after formation. For example, the anhydride oligomer can be incorporated into the microspheres by combining a finely ground dispersion of particles of oligomer in a solution or dispersion with the polymer before forming the microsphere via methods such as those described below. Alternatively, the oligomer compound can be incorporated into the polymer after formation of the microsphere, for example by dispersing the microsphere in a solution or dispersion of the oligomer compound and then removing the solvent by evaporation or filtration.

A. Solvent Evaporation

Methods for forming microspheres using solvent evaporation techniques are described in E. Mathiowitz et al., *J. Scanning Microscopy*, 4:329 (1990); L. R. Beck et al., *Fertil. Steril.*, 31:545 (1979); and S. Benita et al., *J. Pharm. Sci.*, 73:1721 (1984), the disclosures of which are incorporated herein by reference. The polymer and oligomer are dissolved in a volatile organic solvent, such as methylene chloride. A substance to be incorporated optionally is added to the solution, and the mixture is suspended in an aqueous solution that contains a surface active agent such as poly(vinyl alcohol). The resulting emulsion is stirred until most of the organic solvent evaporated, leaving solid microspheres. Microspheres with different sizes (1–1000 microns) and morphologies can be obtained by this method. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

B. Hot Melt Microencapsulation

Microspheres can be formed from polymers such as polyesters and polyanhydrides using hot melt microencapsulation methods as described in Mathiowitz et al., *Reactive Polymers*, 6:275 (1987), the disclosure of which is incorporated herein by reference. In this method, the use of polymers with molecular weights between 3–75,000 daltons is preferred. In this method, the polymer first is melted and then mixed with the solid particles of a substance to be incorporated that have been sieved to less than 50 microns. The oligomer can either be melted with the polymer or else included as fine particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns are obtained with this method.

C. Solvent Extraction

This technique is primarily designed for polyanhydrides and is described, for example, in PCT WO 93/21906, published Nov. 11, 1993, the disclosure of which is incorporated herein by reference. In this method, the substance to be incorporated and the oligomer are dispersed or dissolved in a solution of the selected polymer in a volatile organic solvent like methylene chloride. This mixture is suspended by stirring in an organic oil, such as silicon oil, to form an emulsion. Microspheres that range between 1–300 microns can be obtained by this procedure.

D. Spray-Drying

Methods for forming microspheres using spray drying techniques are described in U.S. Ser. No. 08/467,811, filed Aug. 7, 1995, the disclosure of which is incorporated by reference. In this method, the polymer and oligomer are dissolved in an organic solvent such as methylene chloride. Alternately, if the oligomer is not soluble in the polymer solvent, the oligomer can be micronized, dispersed and sprayed with the polymer solution. A known amount of a substance to be incorporated is suspended (insoluble agent) or co-dissolved (soluble agent) in the polymer solution. The solution or the dispersion then is spray-dried. Microspheres ranging between 0.1–10 microns are obtained. This method is useful for preparing microspheres for imaging of the intestinal tract. Using the method, in addition to oligomers, diagnostic imaging agents such as gases can be incorporated into the microspheres.

E. Phase Inversion

Microspheres can be formed from polymers using a phase inversion method wherein a polymer and oligomer are dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the *dissolved polymer to form small spherical particles, with a narrow size distribution optionally incorporating a drug or other substance.

Advantageously, an emulsion need not be formed prior to precipitation. The process can be used to form microspheres from thermoplastic polymers such as those listed in the following table:

TABLE 1

| Polymer | MW | Conc | Visc | Solvent | Non-Solvent | Product |
| --- | --- | --- | --- | --- | --- | --- |
| polystyrene | 50 kDa | 1% | | methylene chloride | petroleum ether | 500 nm–2 $\mu$m |
| polystyrene | 50 kDa | 3% | | methylene chloride | petroleum ether | 1–2 $\mu$m |
| polystyrene | 50 kDa | 5% | | methylene chloride | petroleum ether | 1–4 $\mu$m |
| polystyrene | 50 kDa | 10% | | methylene chloride | petroleum ether | 1–5 $\mu$m |
| polystyrene | 50 kDa | 15% | | methylene chloride | petroleum ether | 1–10 $\mu$m & aggregates |
| polystyrene | 50 kDa | 20% | | methylene chloride | petroleum ether | large aggregates |

TABLE 1-continued

| Polymer | MW | Conc | Visc | Solvent | Non-Solvent | Product |
|---|---|---|---|---|---|---|
| polystyrene | 50 kDa | 1% | | methylene chloride | ethanol | <100 nm |
| polystyrene | 50 kDa | 5% | | methylene chloride | ethanol | <100 nm |
| polystyrene | 50 kDa | 10% | | methylene chloride | ethanol | 100 nm–3 $\mu$m |
| polycaprolactone | 72 kDa | 1% | 3.188 | methylene chloride | petroleumn ether | 1–3 $\mu$m |
| polycaprolactone | 72 kDa | 5% | 7.634 | methylene chloride | petroleum ether | large aggregates |
| polycaprolactone | 112 kDa | 1% | 4.344 | methylene chloride | petroleum ether | aggregates |
| polycaprolactone | 112 kDa | 5% | | methylene chloride | ethanol | large aggregates |
| polyvinylphenol | 1.5–7 kDa | 1% | | acetone | petroleum ether | 250 nm–1 $\mu$m |
| polyvinylphenol | 1.5–7 kDa | 5% | | acetone | petroleum ether | 1–2 $\mu$m |
| polyvinylphenol | 1.5–7 kDa | 10% | | acetone | petroleum ether | 1–5 $\mu$m |
| polyvinylphenol | 9–11 kDa | 1% | | acetone | petroleum ether | 100 nm–2 $\mu$m |
| polyvinylphenol | 9–11 kDa | 5% | | acetone | petroleum ether | 250 nm–2.5 $\mu$m |
| polyvinylphenol | 9–11 kDa | 10% | | acetone | petroleum ether | 500 nm–10 $\mu$m |
| polylactic acid | 2 kDa | 1% | 0.876 | methylene chloride | petroleum ether | 100 nm |
| polylactic acid | 2 kDa | 5% | 1.143 | methylene chloride | petroleum ether | 500 nm–2 $\mu$m |
| polylactic acid | 2 kDa | 10% | 2.299 | methylene chloride | petroleum ether | 1–10 $\mu$m |
| polylactic acid | 24 kDa | 1% | 1.765 | methylene chloride | petroleum ether | 100 nm |
| polylactic acid | 24 kDa | 5% | 2.654 | methylene chloride | petroleum ether | 500 nm–1 $\mu$m |
| polylactic acid | 24 kDa | 10% | 3.722 | methylene chloride | petroleum ether | 10 $\mu$m & aggregates |
| polylactic acid | 100 kDa | 1% | 2.566 | methylene chloride | petroleum ether | 100 nm |
| polylactic acid | 100 kDa | 5% | 4.433 | methylene chloride | petroleum ether | 0.5–2 $\mu$m & aggregates |
| polylactic acid | 100 kDa | 10% | 8.256 | methylene chloride | petroleum ether | film & aggregates |
| ethylenevinyl acetate | 55 kDa | 1% | | methylene chloride | petroleum ether | globular strands |
| ethylenevinyl acetate | 55 kDa | 5% | | methylene chloride | petroleum ether | coalesced strands |
| ethylenevinyl acetate | 55 kDa | 10% | | methylene chloride | petroleum ether | continuous sheet |
| Poly(acrylonitrile-co-vinyl chloride) | >100 kDa | 1% | 2.566 | acetone | petroleum ether | 1–20 $\mu$m |
| Poly(acrylonitrile-co-vinyl chloride) | >100 kDa | 5% | 15.903 | acetone | petroleum ether | 100 $\mu$m & aggregates |

Table One shows the results of phase inversion experiments including: correlation of polymer species, molecular weight, concentration, viscosity, solvent:non-solvent pairs and final product morphology. Viscosity units are centipoise and concentration units are (w/v) referring to initial polymer concentration.

F. Protein Microencapsulation

Protein microspheres can be formed by phase separation in a non-solvent followed by solvent removal as described in U.S. Pat. No. 5,271,961 to Mathiowitz et al., the disclosure of which is incorporated herein by reference. Proteins which can be used include prolamines such as zein. Additionally, mixtures of proteins or a mixture of proteins and a bioerodable material polymeric material such as a polylactide can be used. In one embodiment, a prolamine solution and a substance to be incorporated are contacted with a second liquid of limited miscibility with the proline solvent, and the mixture is agitated to form a dispersion. The prolamine solvent then is removed to produce stable prolamine microspheres without crosslinking or heat denaturation. Other prolamines which can be used include gliadin, hordein and kafirin. Substances which can be incorporated in the microspheres include, in addition to the oligomer compound, pharmaceuticals, pesticides, nutrients and imaging agents.

G. Low Temperature Casting of Microspheres

Methods for very low temperature casting of controlled release microspheres are described in U.S. Pat. No. 5,019,400 to Gombotz et al., the disclosure of which is incorporated herein by reference. In the method, a polymer is dissolved in a solvent together with a dissolved or dispersed substance to be incorporated and the anhydride oligomer, and the mixture is atomized into a vessel containing a liquid non-solvent at a temperature below the freezing point of the polymer-substance solution, which freezes the polymer droplets. As the droplets and non-solvent for the polymer are warmed, the solvent in the droplets thaws and is extracted into the non-solvent, resulting in the hardening of the microspheres.

In addition to the oligomer compound, biological agents such as proteins, short chain peptides, polysaccharides, nucleic acids, lipids, steroids, and organic and inorganic drugs can be incorporated into the microspheres. Polymers which can be used to form the microspheres include but are not limited to poly(lactic acid), poly(lactic-co-glycolic acid), poly(caprolactone), polycarbonates, polyamides and polyanhydrides. The microspheres produced by this method are generally in the range of 5 to 1000 micrometers, preferably between about 30 and 50 micrometers and also 0.1 to 5 micrometers.

H. Double Walled Microcapsules

Multiwall polymer microspheres may be prepared by dissolving two hydrophilic polymers in an aqueous solution. A substance to be incorporated and the oligomer are dispersed or dissolved in the polymer solution, and the mixture is suspended in a continuous phase. The solvent then is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

Multilayer polymeric drug, protein, or cell delivery systems can be prepared from two or more hydrophilic polymers using the method. Any two or more different biodegradable, or non-degradable, water soluble polymers which are not soluble in each other at a particular concentration as dictated by their phase diagrams may be used. The multilayer microcapsules have uniformly dimensioned layers of polymer and can incorporate a range of substances in addition to the metal compound including biologically active agents such as drugs or cells, or diagnostic agents such as dyes.

Microspheres containing a polymeric core made of a first polymer and a uniform coating of a second polymer, and a substance incorporated into at least one of the polymers, can be made as described in U.S. Pat. No. 4,861,627, the disclosure of which is incorporated herein by reference.

I. Hydrogel Microspheres

Microspheres made of gel-type polymers, such as alginate, are produced through traditional ionic gelation techniques. The polymer first is dissolved in an aqueous solution, mixed with a substance to be incorporated, and the anhydride oligomer, and then extruded through a microdroplet forming device, which in some instances employs a flow of nitrogen gas to break off the droplet. A slowly stirred ionic hardening bath is positioned below the extruding device to catch the forming microdroplets. The microspheres are left to incubate in the bath for twenty to thirty minutes in order to allow sufficient time for gelation to occur. Microsphere particle size is controlled by using various size extruders or varying either the nitrogen gas or polymer solution flow rates.

Chitosan microspheres can be prepared by dissolving the polymer in acidic solution and crosslinking it with tripolyphosphate. Carboxymethyl cellulose (CMC) microspheres can be prepared by dissolving the polymer in acid solution and precipitating the microsphere with lead ions. Alginate/ polyethylene imide (PEI) can be prepared in order to reduce the amount of carboxylic groups on the alginate microcapsule. The advantage of these systems is the ability to further modify their surface properties by the use of different chemistries. In the case of negatively charged polymers (e.g., alginate, CMC), positively charged ligands (e.g., polylysine, polyethyleneimine) of different molecular weights can be ionically attached.

Micronized oligomer particles can be mixed with the hydrogel solution before gelation or else the hydrogel microspheres may be lyophilized and coated with the oligomer solution by dipping or spraying.

J. Incorporation of Dyes

In another embodiment of the invention, dyes may be incorporated either as micronized solid particles, emulsified in oily or watery carriers and dispersed in the polymer matrix or else solubilized in the polymer solvent to effect dispersion in the bulk polymer phase. Dyes may also be immobilized to the surface of the polymer using conventional coupling chemistries, using, for example, glutaraldehyde or carbodiimide, and other coupling methods known to those skilled in the art, to increase bioadhesive properties of polymeric delivery systems.

Modification of Microspheres

Optionally, the polymeric microspheres incorporating an anhydride oligomer may also have incorporated on the surface, either covalently or non-covalently, a targeting molecule to promote specific binding and delivery of the microsphere. Molecules which alter bioadhesive properties of the polymer also may be attached to the microspheres.

For example, the polymers can be modified by increasing the number of carboxylic groups accessible during biodegradation, or on the polymer surface. The polymers can also be modified by binding amino groups to the polymer. The polymers can be modified using any of a number of different coupling chemistries available in the art to covalently attach ligand molecules with bioadhesive properties to the surface-exposed molecules of the polymeric microspheres.

Lectins can be covalently attached to microspheres to target the mucin and mucosal cell layer. Useful lectin ligands include lectins isolated from: *Abrus precatroius, Agaricus bisporus, Anguilla anguilla, Arachis hypogaea, Pandeiraea simplicifolia*, and *Bauhinia purpurea*.

The attachment of any positively charged ligand, such as polyethyleneimine or polylysine, to any microsphere may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microspheres with the appropriate chemistry, such as CDI, and be expected to influence the binding of microspheres to the gut. For example, polyclonal antibodies raised against components of mucin or else intact mucin, when covalently coupled to microspheres, would provide for increased bioadhesion. Similarly, antibodies directed against specific cell surface receptors exposed on the lumenal surface of the intestinal tract would increase the residence time of beads, when coupled to microspheres using the appropriate chemistry. The ligand affinity need not be based only on electrostatic charge, but other useful physical parameters such as solubility in mucin or specific affinity to carbohydrate groups.

The covalent attachment of any of the natural components of mucin in either pure or partially purified form to the microspheres would decrease the surface tension of the bead-gut interface and increase the solubility of the bead in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, such as polyaspartic acid and polyglutamic acid, may also increase bioadhesiveness. Using polyamino acids in the 15,000 to 50,000 kDa molecular weight range would yield chains of 120 to 425 amino acid residues attached to the surface of the microspheres. The polyamino chains would increase bioadhesion by means of chain entanglement in mucin strands as well as by increased carboxylic charge.

Therapeutic and Diagnostic Agents

Polymers incorporating an anhydride oligomer which improves the bioadhesive properties of the polymer can be used to form, or to coat, drug delivery systems such as microspheres or tablets containing any of a wide range of therapeutic and diagnostic agents. The drug delivery systems can be administered by, e.g., oral, rectal, nasal or vaginal administration.

In one embodiment, the polymers incorporating the oligomer may be used to form bioadhesive microspheres containing a drug which is either dispersed throughout the polymer or dispersed within one or more areas within the microsphere. Any of a wide range of materials can be incorporated into the microspheres including organic compounds, inorganic compounds, proteins, polysaccharides, and nucleic acids, such as DNA and RNA, using standard techniques. Examples of useful proteins include hormones such as insulin, growth hormones including somatometins, transforming growth factors, and other growth factors, antigens for oral vaccines, enzymes such as lactase or lipases, and digestive aids such as pancreatin. The polymers incorporating the oligomer and the diagnostic or therapeutic agent also may be formulated as a tablet using methods available in the art.

The incorporation of the anhydride oligomer into polymers increases their ability to bind to mucous membranes. The incorporation of organic dyes into polymers also increases their bioadhesive properties. Thus, the incorporation of oligomers or organic dyes into the polymers can enhance the adhesion of the polymers to mammalian mucous membranes including the entire gastrointestinal tract, respiratory, excretory and reproductive tracts, and thus can enhance the delivery of drugs incorporated into the polymers. The drug delivery systems thus can be used for gastrointestinal, vaginal or respiratory delivery of a preselected drug or diagnostic agent. Polymers in the form of, for example, microspheres can be administered in a pharmaceutically acceptable carrier as, for example, a suspension or ointment to the mucosal membranes, via, e.g., the nose, mouth, rectum, or vagina. Pharmaceutically acceptable carriers for example for oral or topical administration are known and determined based on compatibility with the polymeric material. Other carriers include bulking agents such as Metamucil™.

Therapeutic or diagnostic agents which can be incorporated into microspheres or other drug delivery systems for application to the vaginal lining or other mucosal membrane lined orifices such as the rectum include spermacides, yeast or trichomonas treatments and anti-hemorrhoidal treatments. The oligomer-containing polymers can be used in any muco-adherent delivery system including gastrointestinal delivery and vaginal delivery systems. For example, the polymers incorporating a oligomer compound can be used to improve adhesion of vaginal rings used for delivery of contraceptives or hormones, or to improve the residence time of osmotic pumps. Microspheres also may be formulated for adhesion and delivery of chemotherapeutic agents to tumor cells.

Polymeric materials such as microspheres incorporating oligomer compounds which promote bioadhesiveness are useful for the oral administration of a wide range of drugs, such as sulfonamides (e.g., sulfasalazine) and glycocorticoids (e.g., bethamethasone) used for treatment of bowel diseases. Examples of other useful drugs include ulcer treatments such as Carafate™ from Marion Pharmaceuticals, neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Testred (methyltestosterone) from ICN Pharmaceuticals, and antiparasitics such as mebendzole (Vermox™, Jannsen Pharmaceutical), and growth factors such as fibroblast growth factor ("FGF"), platelet derived growth factor ("PDGF"), epidermal growth factor ("EGF"), and transforming growth factor-beta ("TGF-beta").

Polymeric microspheres incorporating a oligomer to enhance bioadhesion, and a drug such as sulfasalazine are especially useful for treatment of inflammatory bowel diseases such as ulcerative colitis and Crohn's disease. In ulcerative colitis, inflammation is restricted to the colon, whereas in Crohn's disease, inflammatory lesions may be found throughout the gastrointestinal tract, from the mouth to the rectum. Sulfasalazine is one of the drugs that is used for treatment of these diseases. Sulfasalazine is cleaved by bacteria within the colon to sulfapyridine, an antibiotic, and to 5-amino salicylic acid, an anti-inflammatory agent. The 5-amino salicylic acid is the active drug and it is needed locally. The polymeric drug delivery systems can improve the therapy by retaining the drug for a prolonged time in the intestinal tract. For Crohn's disease, retention of 5-aminosalicylic acid in the upper intestine is of great importance, since bacteria cleave the sulfasalazin in the colon, and the usual way to treat inflammations in the upper intestine is by local administration of 5-aminosalicylic acid.

The polymeric microspheres also may be used for oral vaccines. Microspheres incorporating antigens for use as a vaccine can be fabricated to have different retention times in the gastrointestinal tract. The different retention times, among other factors, can stimulate production of more than one type (IgG, IgM, IgA, IgE, etc.) of antibody.

The size of the microspheres can be selected to optimize microsphere uptake, alone or in combination with other factors, including polymer composition. As used herein, the term "microspheres" is defined as polymeric particles or capsules having a diameter on the order of 5 mm (5000 microns) or less, including particles or capsules having a diameter less than 1 mm, in the micrometer scale, or, for example, less than 1000 nm, in the nanometer scale, for example 100–1000 nanometers.

In one embodiment, microspheres with a diameter less than about 10 microns may be used. Enhanced uptake is achieved if the polymeric microspheres are loaded with oligomers and fabricated to be smaller than 3 μm. In one embodiment, microspheres with a diameter between about 2 to 5 microns can be used, to enhance uptake into gut-associated lymphoid tissue, in particular into lymphatic cells and phagocytic cells. Additionally, microspheres less than about 2 microns, or optionally, less than about 1 micron in diameter, can be used, to enhance uptake by non-lymphatic cells and non-phagocytic cells. To reduce uptake, microspheres having a diameter greater than 10 microns can be used, for example, to enhance delivery of a drug or diagnostic agent in the microspheres to the gastrointestinal tract.

Oligomer-containing or dye-containing polymers also can be used to coat or form micradio-opaque mate oral or intravenous administration of radio-opaque materials for use in imaging. In a preferred method for imaging, a radio-opaque material such as barium is coated with the polymer having the metal compound incorporated therein. Examples of other radio-opaque materials include gases or gas emitting compounds. Other radioactive materials or magnetic materials can be used in place of, or in addition to, the radio-opaque materials.

Polymers incorporating anhydride oligomers or dyes also may be used to form or coat systems used as a perivascular treatment to prevent restenosis of blood vessels following balloon angioplasty. The oligomer-containing systems may be implanted outside damaged blood vessel walls and the bioadhesive properties used to retain the systems at the implant site and deliver anti-proliferative or thrombolytic drugs to the vessel wall, as described by E. Edelman et al., *Proc. Natl. Acad. Sci.*, USA 30:1513–1517 (1993).

The polymers incorporating an anhydride oligomer or a dye also can be used in applications for controlled release of anti-arrhythmic agents. R. Levy et al., *J. Pharm. Sci.*, 83:156–1643 (1994) describes the use of non-bioadhesive polymeric implants attached to the heart for delivery of drugs to prevent arrthymias. Bioadhesive microspheres incorporating anhydride oligomers may be used to deliver growth factors or other bioactive drugs to the heart in a site-specific manner after attachment to the pericardial sac. The delivery of bioactive drugs to the heart using alginate microspheres has been described by K. Harada et al.,*J. Clin. Invest.*, 94:623–630 (1994).

Drug Delivery Devices

The bioadhesion of any of a wide range of different polymeric drug delivery systems can be enhanced by the incorporation of the anhydride oligomer compounds into the polymer. In one embodiment, polymers incorporating a oligomer compound can be used to form microsphere delivery systems or used to coat pre-existing microspheres. Films, coatings and other systems also can be formed from polymers incorporating a oligomer to improve the bioadhesiveness of the systems. For example, a coating of a polymer incorporating a oligomer compound can be coated on controlled-release drug delivery systems ranging from micrometer sized microspheres to millimeter sized pumps such as osmotic pumps, or on delivery systems such as vaginal rings. The bioadhesiveness of the systems thus can be improved and therefore their effectiveness in drug delivery applications can be enhanced.

The films and coatings can be formed using methods available in the art, including, for example, film casting, extrusion, melt casting, pressing, molding, and coating techniques such as pan coating. In one embodiment, for example, the oligomer compounds can be incorporated into coatings applied by fluidized beds for the coating of large tablets. The benefits of bioadhesive drug delivery systems include increased bioavailability, the protection of labile drugs from inactivation by digestive enzymes or other hydrolytic processes, and increased patient compliance because of reduced dosing regimens. The invention will be further understood from the following non-limiting examples.

EXAMPLE 1

Insulin Delivery in Nanoparticles Produced by Phase Inversion

Nanoparticles were produced by a phase inversion process. Fumaric acid was purchased from Fisher Chemical, and recrystallized once from a 5% solution in 95% ethanol. The fumaric acid was polymerized by refluxing for about 3.5 hr in acetic anhydride (20 g per 250 mL). After reflux, the excess acetic anhydride was removed by evaporation under vacuum, and stored at 4° C. overnight. Excess liquid acetic acid was removed via filtration if necessary, and the retentate was purified by dissolving in toluene with heat. The resulting solution then was filtered while warm, and the retentate discarded. The filtrate was allowed to crystallize at 4° C. overnight, and then washed with ether two times to remove any remaining toluene. The fumaric acid oligomer precipitate (FAPP), 240–280 MW, was collected by filtration, dried under vacuum, and stored at –20° C. in a sealed amber glass jar.

Subsequently, 0.1 g of the fumaric acid oligomer (FAPP) and 0.2 g of poly(lactide-co-glycolide) (PLGA, 50:50) were dissolved in 10 mL methylene chloride. 0.022 grams of micronized FeO were added to the polymer solution.

20 mg of zinc-insulin (U.S. Biochemicals) was added to 1.0 ml of 100 mM Tris, pH 10.0, 0.25 ml of 0.3 N HCl was added to dissolve the insulin, resulting in a solution with a pH of 5.5, and an additional 0.75 ml deionized water was added to this solution, which remained clear. The final insulin concentration was 10 mg/mL. 50 ml of 10% $ZnSO_4$ was added to 0.5 mL of the insulin solution, causing crystals to form.

The zinc-insulin suspension then was added to the polymer solution and emulsified using a Virtis-shear mixer at the highest setting. This mixture was quickly dispersed into 1 L of petroleum ether. The nanospheres (less than one micrometer) were collected by vacuum filtration, air dried, frozen with liquid nitrogen and lyophilized for 24 hours. The FeO in the resulting FAPP/PLGA microspheres also provided an electron dense tracer for Transmission Electron Microscopic ("TEM") visualization.

The FAPP/PLGA nanospheres released insulin over a three day period. An in vitro release study of nanospheres loaded with 1.6% insulin (w/w) showed that 60% of insulin was released within 2 hours, and that 95% was released within 72 hours. To insure that the encapsulated insulin was not deactivated by the fabrication processing, 25 mg of the nanospheres were I.P. injected in PBS into two, fasted 300 g rats, and blood samples from the rat tail vein were tested at 1.5, 4 and 6 hrs post injection. The average fasting blood glucose level was 87–0.5 mg/dL. After 1.5 hrs the level fell to 48±2 mg/dL, after 4 hrs the level was 8±0.5 mg/dL, and after 6 hrs, the level increased to 38±14 mg/dL.

In Vivo Study

The delivery of insulin after administration of the nanoparticles, loaded with 10% (w/w) micronized FeO, was studied in a rat model. Five 300 g 22 hr. fasted rats were anesthetized with Metofane and fed the following formulations by stomach tube:

Rats 1 and 2: 0.5 mL saline

Rat 3: 24 I.U. insulin/0.5 mL saline (amorphous suspension)

Rats 4 and 5: 50 mg FAPP/PLGA nanospheres containing 20 I.U. insulin and 10% (w/w)FeO Blood samples from the tail vein were taken as an initial baseline and rats were subsequently tested for glucose tolerance following injection of a subcutaneous glucose load, consisting of 5 mL of 5% sterile glucose solution. Tutwiler et al., *Diabetes*, 27:856–867 (1978). At 1, 3, 4 and 5 hours postfeeding, blood samples were again taken and plasma glucose levels were measured spectrophotometrically at 505 nm using the Trinder glucose assay. The glucose levels normalized to fasting blood glucose baseline levels over time are shown in FIG. 1.

The negative controls, rats 1 and 2, showed expected responses to the glucose load. Blood glucose levels rose by 35% and 31% and then began dropping back to baseline. Rat number 3, which received an oral insulin solution, showed a greater increase in serum glucose level (62% by 3 hours) and then also returned to baseline indicating some very limited bioavailability of unencapsulated insulin.

Rat 5 had only a 4% increase in blood sugar by 3 hours and then the glucose levels dropped to below baseline. Rat 4 had very high fasting glucose level and also had very erratic measured blood levels and died after 5 hours.

The rats fed insulin-loaded nanospheres appeared to be better able to control a glucose load than the rats not given the nanospheres (4% increase at 3 hours as opposed to ~30% increase), thus implying uptake and activity of the encapsulated insulin. Additionally, at 5 hours, only the rats fed the insulin spheres showed blood glucose levels significantly below baseline fasting levels.

Light microscopic examination of tissue samples from Rat 4 taken after 5 hrs demonstrated a widespread distribution of insulin-loaded nanospheres. The spheres were observed in great numbers, traversing the mucosal epithelium in the small intestine, Peyers' Patches ("PP"), lamina propria, lacteals, blood vessels of the gut wall and also in spleen and tissue samples.

EXAMPLE 2

Hot Melt Fabrication of Oligomer Microspheres

Fumaric acid and sebacic acid (Fisher Scientific) were recrystallized from 5% solutions of the monomers in 95% ethanol. The monomers was separately polymerized by refluxing for 0.5–3.5 hrs in acetic anhydride (20 g per 250 mL) and excess acetic anhydride was removed by vacuum evaporation and stored overnight at 4° C. Increasing the duration of reflux increased the molecular weight of the oligomers. Excess acetic acid was removed via filtration if necessary, and the retentate was purified by dissolution in warm toluene. The solution was then filtered, allowed to crystallize at 4° C. overnight and washed twice with petroleum ether to extract residual toluene. The oligomer precipitates (PP) were collected by filtration, dried under vacuum, and stored at −20° C. in a sealed amber glass jar.

For hot melt fabrication of microspheres, the oligomers can either be melted together (FAPP and SAPP) or else combined with other polymers as excipients to improve bioadhesion by melt blending or else inclusion as micronized particles. The mixture is suspended in a non-miscible solvent (like silicon oil) with continuous stirring, and heated to 5° C. above the melting point of the polymer. Once the emulsion is stabilized, the system is cooled to solidify the microspheres. Oil is removed by washing with petroleum ether to give a free-flowing powder, consisting of microspheres with sizes between 0.5 to 1000 μm.

The hot melt procedure was used to make FAPP:SAPP microspheres (92:8 molar) (1:1 w/w) ratio. The spheres appeared highly crystalline and polarized light. SEM showed a rough surface texture without any flakes. Molecular weight averaged 3000 DA and melt temperature as determined by differential scanning calorimetry (DSC) was 63° C.

Various drugs or proteins, such as bovine serum albumin (BSA), may be loaded into the FAPP:SAPP (92:8) microspheres. Hot melt FAPP:SAPP (92:8) microspheres loaded with 10% BSA (w/w) had a white fluffy surface coating, when examined by SEM, which may have been due to crystallization during cooling.

FAPP:SAPP (92:8) microspheres, loaded with 18% acetaminophen (w/w) were fabricated using hot melt. The microspheres were cooled slowly while in the hot oil bath, and stirring was continued overnight. Resulting microspheres averaged 200 μm in diameter.

The molar ratios of FAPP:SAPP may be altered. Hot melt FAPP:SAPP (50:50) microspheres were also manufactured using the procedure described above.

EXAMPLE 3

Bioassay of Adhesion of FAPP:SAPP "Hot Melt" Formulations to Intestinal Mucosa In Vitro An in vitro assay for quantifying bioadhesion of microspheres to intestinal tissue was used to test the hot melt microspheres made as described in Example 2 (Jacob et al., *Proceed,. Intern. Symp. Control. Rel. Bioact. Mater.* 22:312–313 (1995). Everted sac experiments were performed using the microsphere formulations listed above. 6 cm segments of rat jejunum flushed with phosphate buffered saline (PBS), everted and fashioned into sacs filled with PBS. Sacs were incubated with 60 mg of microspheres in 5 ml of PBS at 37° C. with end-over-end agitation. After 30 min, the sacs were removed and the unbound microspheres were collected, washed with distilled water, frozen and lyophilized for 24 hrs. The weight of unbound beads was used to determine the amount of beads bound to the intestine:

| Formulation | % bound |
| --- | --- |
| FAPP:SAPP (92:8) hot melt | 75 ± 4 |
| FAPP:SAPP (50:50) hot melt | −19* ± 3 |
| SAPP hot melt | 51 ± 5 |
| FAPP:SAPP (92:8) 50% tonopaque HM | 27 ± 8 |
| Polycaprylactone (72 kDa:32 kDa::1:1) HM + 14% fumaric acid monomer (w/w) | 14 ± 4 |
| Polycaprylactone (72 kDa:32 kDa::1:1) | 9 ± 4 |

*The microspheres were bound to the mucus and sloughed off the intestinal sac, suggesting the microsphere-mucus attachment was stronger than the mucus-tissue bond strength.

Polycaprylactone (PCL) was included as a negative control for bioadhesion. The inclusion of fumaric acid monomer into PCL spheres had very little effect on improving the bioadhesion of PCL spheres.

FAPP:SAPP (92:8) with 50% tonopaque microspheres were manufactured and appeared brown in color while microspheres without tonopaque were white/tan in color.

The Tonopaque beads caused copious mucus secretion (beads were bound to mucus and sloughed off the intestinal sac. The pure oligomer beads bound to mucus and remained on the intestinal sac.

To further investigate the mucus secretion phenomenon, everted sacs were incubated for 60 minutes and examined at intervals. Smaller FAPP:SAPP (92:8) (with 50% Tonopaque) microspheres (<200 microns) adhered to the tissue for the entire 60 minutes. Larger microspheres (200–600 microns) adhered in great number to the mucosa for 15 minutes, caused mucus secretion and were sloughed off with the mucus during the remaining 45 minutes.

EXAMPLE 4

In vitro Bioavailability of Acetaminophen from Oligomer Microspheres

The FAPP:SAPP 92:8 18% acetaminophen microspheres were made using the hot melt method described in Example 2, and were used in everted sac experiments and the release of drug was determined to yield information on bioavailability. The release was determined by homogenizing intestinal tissue and mucosal and serosal fluids. The homogenates were centrifuged and the supernatant fluids were assayed for acetaminophen.

The distribution of acetaminophen (mg/dl) in tissue compartments after incubation of everted intestine in vitro is shown below:

|  | mucosal fluid | serosal fluid | gut wall |
| --- | --- | --- | --- |
| encapsulated | 12 ± 2 | 5 ± 1 | 27 ± 4 |
| control | 39 ± 1 | 13 ± 1 | 19 ± 7 |

|  | mucosal/serosal ratio |
| --- | --- |
| encapsulated | 2.5 |
| control | 3.0 |

Although less acetaminophen was transported from the mucosal fluid (gut lumen compartment) into the serosal fluid (blood compartment) for the encapsulated samples, the amount of drug in the gut wall was higher with less of the drug appearing in the mucosal compartment. A lower encapsulated Mucosal/Serosal ratio would indicate more efficient release through the gut wall and into the serosal fluid than into the surrounding mucosal fluid.

An analysis was also performed on the everted sac experiments using FAPP:SAPP (92:8) loaded with 18% acetaminophen. More acetaminophen stayed in the gut wall rather than going into the mucosal or serosal fluid. The analysis of acetaminophen distribution (% of total dose) for encapsulated and control dosage forms is shown below:

|  | mucosal fluid | serosal fluid | gut wall |
| --- | --- | --- | --- |
| encapsulated | 53.0 ± 13.7 | 2.2 ± 0.4 | 44.8 ± 13.5 |
| control | 86.5 ± 1.5 | 5.7 ± 0.9 | 7.9 ± 0.9 |

The average recovery of acetaminophen was 93.9±3.0% (n=8). Clearly, the encapsulated drug was retained in proximity with the GI mucosa rather than being released into either the mucosal or serosal compartments.

EXAMPLE 5

Phase Inversion Fabrication of Oligomer Nanospheres

Oligomers (FAPP:SAPP) were also formed into nanospheres using the phase inversion method. In the method, a polymer and oligomer, or mixture of oligomers are dissolved in a "good" solvent and micronized particles of the substance to be encapsulated, including the oligomer and a drug additive, are mixed or suspended in the polymer solution. The mixture is poured into a strong non-solvent for the polymer, to spontaneously produce, under favorable conditions, polymeric nanospheres, wherein the polymer is either coated with the particles or the particles are dispersed in the polymer. The method can be used to produce microparticles in a wide range of sizes from about 10 nm to 10 $\mu$m.

Specifically, a 5% w/v solution of FAPP (MW=240–280) in acetone was mixed acetone was mixed with a 5% w/v solution of SAPP (MW=3000–4000) in methylene chloride to yield a 1:1 w/w ratio of oligomers (92:8 molar ratio). When mixed, the two solutions remained miscible. 10 ml of the mixed solution was precipitated into 400 ml of petroleum ether. The resulting precipitate was collected by filtration and air-dried. Microsphere size ranged from 0.1–5 microns.

EXAMPLE 6

Solvent Extraction Fabrication of Oligomer Microspheres Containing a Base Polymer Oligomer was prepared as described in Examples 1 and 2. Solvent extraction microspheres of FAPP:SAPP:PLA (91.5:8.2:0.3) (molar ratios) were prepared by mixing a 5% (w/v) solutions of FAPP (MW=240–280) in acetone with a 5% (w/v) solution of SAPP (MW=3000–4000) in methylene chloride to yield a 1:1 w/w ratio of oligomers. 10 ml of the oligomer solution was used to dissolve 0.5 g of poly-lactic acid (PLA, MW=24 kDa). The PLA was added as a base polymer to increase the hardness of the microspheres. The solution was dripped into 200 ml of mineral oil with 5 drops of SPAN-85 surfactant and stirred for 14 hours. The resulting spheres were 100 $\mu$m in average diameter.

The preparation of solvent extraction FAPP:SAPP:PLA (91.5:8.2: 0.3) microspheres with 10% BSA was accomplished by using solution above mixed with 0.4 g micronized BSA (particle size range was 1–100 $\mu$m; average was approximately 30 $\mu$m) and dripped into corn oil with 3 drops of SPAN 85 land stirred for 14 hours.

Microspheres containing FAPP and PLA 24 kDa without SAPP were also fabricated by solvent removal. The microspheres were loaded with 12% BSA (w/w) as micronized particles (average size 30 $\mu$m, range 1–100 $\mu$m) 0.18 gm of FAPP (MW=240–280) (0.9 mmol) in 1 ml of acetone was mixed with 2.4 gm of PLA 24 kDa (0.1 mmol) in 24 ml of methylene chloride. Five ml of the mixture was mixed with 70 mg of micronized BSA and dispersed in 200 ml mineral oil with 3 drops of SPAN 85. The emulsion was continuously stirred with an overhead stirrer for 14 hrs at a rate of 600 rpm. Resulting spheres were double walled with BSA loaded randomly throughout shell and core and were approximately 100 $\mu$m in average diameter.

EXAMPLE 7

Phase Inversion Fabrication of Oligomer Nanospheres Containing a Base Polymer

Nanospheres containing FAPP:SAPP:PLA (91.5:8.2:0.3) (molar ratios) were manufactured using the phase inversion technique. Five ml aliquots of 5% FAPP (MW=240–280) (w/v) in acetone and 5% SAPP (MW=3000–4000) (w/v) in methylene chloride were mixed yielding a 1:1 w/w ratio of oligomers. When mixed, the two solutions remained miscible. 0.2 g of PLA (24 kDa) was added yielding a oligomer solution containing 2% PLA (w/v). PLA was added as a base polymer to increase the hardness of the final microspheres. The solution was dispersed into 400 ml of petroleum ether (non-solvent).

Nanospheres composed of FAPP:PLA (24 kDa) in a 90:10 molar ratio were fabricated using the phase inversion technique. A stock solution was prepared by mixing 0.18 gm of FAPP (0.9 mmol) in 1 ml of acetone with 2.40 g of PLA 24 kDa (0.1 mmol) in 24 ml of methylene chloride. Five ml of the mixture was dispersed into 400 ml of petroleum ether, recovered by filtration and air-dried.

FAPP:PLA (24 kDa) (90:10) nanospheres loaded with 10% micronized BSA (w/w) were prepared using the phase inversion technique. Five ml of a stock solution, prepared by mixing 0.18 gm of FAPP (0.9 mmol) in 1 ml of acetone with 2.40 g of PLA 24 kDa (0.1 mmol) in 24 ml of methylene chloride, was used to suspend 57 mg of micronized BSA. The protein-polymer mixture was dispersed into 400 ml of petroleum ether, recovered by filtration and air-dried.

A control formulation of PLA 24 kDa nanospheres were fabricated using the phase inversion technique. Five ml of a 5% PLA 24 kDa in methylene chloride (w/v) was dispersed into 400 ml of petroleum ether, recovered by filtration and air-dried.

Everted sac experiments were performed utilizing the phase inverted microspheres from the above formulation. Results of this bioassay indicated adhesion ranging from 26–42%. It is not known if the oligomers were incorporated on the surface of the microspheres or distributed throughout the microspheres.

EXAMPLE 8

Solvent Evaporation Fabrication of Oligomer Microspheres

FAPP:PLA (24 kDa) (99.95:0.05, m/m; 60:40, w/w) microspheres were fabricated using the solvent evaporation technique. 0.18 gm of FAPP (0.9 mmol) was dissolved in 1 ml of acetone and mixed with 0.12 gm of PLA 24 kDa (0.005 mmol) in 9 ml of methylene chloride. The mixture was dispersed into a stirred bath of 600 ml distilled water, 50 ml of 2% PVA (w/v) and 3 drops of Tween 20. The mixture was stirred for 20 minutes at a rate of 1000 rpm with an overhead stirrer. The spheres were collected by filtration, washed with distilled water and air dried. SEM analysis showed irregular spheres ranging in size from 1–100 μm with rough, porous surface texture.

Solvent evaporation FAPP:PLA (24 kDa (98.9:1.1, m/m; 42.8:57.2, w/w) microspheres were also manufactured. 0.18 gm of FAPP (0.9 mmol) was dissolved in 1 ml of acetone and mixed with 0.24 gm of PLA 24 kDa (0.010 mmol) in 9 ml of methylene chloride. The mixture was dispersed into a stirred bath of 600 ml distilled water, 50 ml of 2% PVA (w/v) and 3 drops of Tween 20. The mixture was stirred for 20 minutes at a rate of 1000 rpm with an overhead stirrer. The spheres were collected by filtration, washed with distilled water and air dried. Spheres ranging in size from 1–100 μm were the final product.

EXAMPLE 9

Degradation of Oligomer Microspheres

Oligomer microspheres manufactured by a hot melt procedure were used in a degradation study to determine the stability of the different oligomer ratios to various storage conditions. Spheres were stored at 4° C. and incubated in an oven at 37° C. for the duration of one month. Two ratios of the FAPP:SAPP mix were used, FAPP:SAPP (92:8) and (50:50). The microsphere samples were collected at various times over the next 29 days. Analysis was performed with a gel permeation chromatograph (GPC), for polymer molecular weight determination, and a Fourier transform infrared spectrometer (FTIR), for chemical bond determination.

The FAPP:SAPP (50:50) microspheres were found to be stable at 4° C. and moderately stable at 37° C., as evidenced by the consistency of the characteristic FTIR scan and molecular weight over time. The FAPP:SAPP (92:8) microspheres were relatively stable at 4° C. but unstable at 37° C., as evidenced by the drop in molecular weight and by the emergence of a carboxylic acid peak at about 1700 cm–1.

EXAMPLE 10

Enhancement of Bioadhesion by Incorporation of Dyes into Microspheres

Bioadhesion forces were quantified using a bioadhesive force transducer previously described by Chickering et al., *J. Control. Release* (1995) 34:251–61. The force transducer utilizes a sensitive microbalance to which a microsphere is attached via a small diameter metal wire. The tissue sample is immersed in physiological saline, buffered to pH 7.4, and placed in a special chamber designed to maintain temperature at 37° C. The tissue chamber sits on a motorized stage and is brought into contact with the polymer microsphere. The microsphere is held in contact with the tissue for seven minutes. Finally, the tissue sample is slowly pulled away from the microsphere and simultaneously force versus position and force versus time data is recorded. For the purpose of these experiments the fracture strength of each microsphere-tissue interaction was calculated and used as the main comparative value. Fracture strength (FS) is a stress value calculated by normalizing peak tensile load (PTL) to microsphere diameter (d):

$$FS = \frac{PTL}{(1/4)\pi d^2}$$

For all experiments described, the tissue used was rat duodenum. Two runs were performed on each 2 cm section of tissue, one each of the control spheres and the dyed spheres.

1. Sudan Red

Sudan Red or Sudan III (1-[[4-(Phenylazo)phenyl]azo]-2-naphthalenol) is a hydrophobic dye with a molecular weight of 352 gm/mol. To test the effect of Sudan Red dye on the adhesion of polystyrene microspheres (400–700 μm) to rat intestinal tissue, microspheres were prepared by a solvent evaporation method. Ten ml of 20% polystyrene 50 kDa (w/v) in methylene chloride containing 10 mg of Sudan Red dye was dispersed in a stirred bath of 600 ml distilled water containing 50 ml of 2% PVA (w/v) and 3 drops of Tween 20. The mixture was stirred for 20 minutes at a rate of 1000 rpm with an overhead stirrer. The spheres were collected by filtration, washed with distilled water and air dried. Spheres ranging in size from 1–1000 μm were collected and sieved. Control spheres were fabricated using the same technique without inclusion of dye.

The observed fracture strengths for the control spheres (no dye) averaged 426±53 mN (n=24). Sudan Red microspheres had an average fracture strength of 199±23 mN (n=24). Consequently, since all other factors were the same, we concluded that incorporation of Sudan dye decreased the average fracture strength by 53%.

2. Azure II

Azure II is a hydrophobic dye including a mixture of methylene blue and methylene azure (an oxidated version of methylene blue). Methylene blue or (3,7-Bis (Dimethylamino)-phenothiazin-5-ium chloride) has a molecular weight of 320 gm/mol. Tensiometer studies with Azure II-loaded spheres resulted in an average fracture strength of 550±95 mN (n=13), or an increase of 29% over the control spheres with no dye.

Modifications and variations of the present invention will be obvious to those skilled in the art from the foregoing detailed description. Such modifications and variations are intended to come within the scope of the following claims.

We claim:

1. A method for improving the bioadhesiveness of a polymer, the method comprising incorporating an anhydride oligomer in the polymer in an amount effective to enhance the ability of the polymer to adhere to a mucosal membrane, wherein the anhydride oligomer includes twenty or fewer diacid units linked by anhydride linkages or has a molecular weight of 5000 Daltons or less, and wherein the anhydride oligomer is incorporated by dispersing solid particles of anhydride oligomer into the polymer, dissolving anhydride oligomer and polymer in a solvent for both the polymer and the oligomer, or blending liquified anhydride oligomer with liquified polymer.

2. The method of claim 1 wherein the anhydride oligomer is associated with the polymer by ionic or covalent bonds.

3. The method of claim 1 wherein the anhydride oligomer comprises dicarboxylic acid monomers selected from the group consisting of fumaric, maleic, succinic, adipic, sebacic and carboxyphenolic acids.

4. The method of claim 1 wherein the anhydride oligomer comprises dicarboxylic acid monomers selected from the group consisting of bis(p-carboxyphenoxy)methane, bis(p-carboxyphenoxy)propane, and bis(p-carboxyphenoxy) hexane, phthalic acid, isophthalic acid, terephthalic acid, azeleic acid, pimelic acid, itaconic acid, cyclohexane dicarboxylic acid, 1,4 phenylene dipropionic acid and 1,10-dodecanedioic acid.

5. The method of claim 1 wherein the polymer is in the form of a microsphere, and wherein the method comprises improving the bioadhesiveness of the microsphere by incorporating the anhydride oligomer in the polymer during formation of the microsphere, thereby to enhance the ability of the microsphere to adhere to a mucosal membrane.

6. The method of claim 5 wherein the anhydride oligomer is in the form of a fine dispersion of particles on at least the surface of the microsphere.

7. The method of claim 5 wherein the polymer incorporating the anhydride oligomer is coated onto the surface of a microsphere formed of a different material.

8. The method of claim 1 wherein the polymer is selected from the group consisting of proteins and polysaccharides.

9. The method of claim 1 wherein the polymer is selected from the group consisting of polyamides, polycarbonates, polyalkylenes, polyaryalkylenes, polyalkylene glycols, polyalkylene oxides, polyalkylene terephthalates, polyvinyl polymers, polyphosphazenes, polyacrylamides, polysiloxanes, polyurethanes, polymers of acrylic and methacrylic acid, celluloses, polyanhydrides, polyesters, poly(hydroxy acids), and blends and copolymers thereof.

10. The method of claim 5 wherein the microsphere further comprises a therapeutic or diagnostic agent.

11. The method of claim 10 wherein the diagnostic agent is selected from the group consisting of gases, gas evolving agents and radio-opaque compounds.

12. The method of claim 1 wherein the polymer defines or coats a drug delivery device containing a therapeutic agent.

13. The method of claim 1 wherein the polymer defines or coats a surgical implant device.

14. The method of claim 5 wherein the microsphere has a diameter greater than or equal to about 10 microns.

15. The method of claim 5 wherein the microsphere has a diameter between about 2 and 5 microns.

16. The method of claim 5 wherein the microsphere has a diameter of less than about 2 microns.

17. The method of claim 5 wherein the microsphere has a diameter less than about 1 micron.

18. A composition comprising a polymer incorporating an anhydride oligomer in an amount effective to improve adhesion of the polymer to a mucosal membrane, wherein the anhydride oligomer includes twenty or fewer diacid units linked by anhydride linkages or has a molecular weight of 5000 Daltons or less, and wherein the anhydride oligomer is incorporated by dispersing solid particles of anhydride oligomer into the polymer, dissolving anhydride oligomer and polymer in a solvent for both the polymer and the oligomer, or blending liquified anhydride oligomer with liquified polymer.

19. The composition of claim 18 wherein the anhydride oligomer is associated with the polymer by ionic interactions or covalent bonds.

20. The composition of claim 18 wherein the anhydride oligomer comprises dicarboxylic acid monomers selected from the group consisting of fumaric, maleic, succinic, adipic, sebacic and carboxyphenolic acids.

21. The composition of claim 18 wherein the polymer is in the form of a microsphere.

22. The composition of claim 21 wherein the anhydride oligomer is in the form of a fine dispersion of particles on at least the surface of the microsphere.

23. The composition of claim 21 wherein the polymer incorporating the anhydride oligomer is coated onto the surface of a microsphere formed of a different material.

24. The composition of claim 18 wherein the polymer is selected from the group consisting of proteins and polysaccharides.

25. The composition of claim 18 wherein the polymer is selected from the group consisting of polyamides, polycarbonates, polyalkylenes, polyaryalkylenes, polyalkylene glycols, polyalkylene oxides, polyalkylene terephthalates, polyvinyl polymers, polyphosphazenes, polyacrylamides, polysiloxanes, polyurethanes, polymers of acrylic and methacrylic acid, celluloses, polyanhydrides, polyesters, poly(hydroxy acids), and blends and copolymers thereof.

26. The composition of claim 21 wherein the microsphere further comprises a therapeutic or diagnostic agent.

27. The composition of claim 26 wherein the diagnostic agent is selected from the group consisting of gases, gas evolving agents and radio-opaque compounds.

28. The composition of claim 18 wherein the polymer defines or coats a drug delivery device containing a therapeutic agent.

29. The composition of claim 21 wherein the microsphere has a diameter greater than or equal to about 10 microns.

30. The composition of claim 21 wherein the microsphere has a diameter of between about 2 to 5 microns.

31. The composition of claim 21 wherein the microsphere has a diameter less than about 2 microns.

32. The composition of claim 21 wherein the microsphere has a diameter less than about 1 micron.

* * * * *

UNITED STATES PATENT AND TRADEMARK OFFICE
CERTIFICATE OF CORRECTION

PATENT NO.   : 5,955,096
DATED        : September 21, 1999
INVENTOR(S)  : Camila A. Santos et al.

It is certified that error appears in the above-identified patent and that said Letters Patent is hereby corrected as shown below:

Column 6,
Line 6, please delete "2,979,578;" and insert in place thereof -- and --
Lines 6 and 7, please delete "; and 2,675,619"

Signed and Sealed this

Seventeenth Day of December, 2002

JAMES E. ROGAN
*Director of the United States Patent and Trademark Office*